(12) United States Patent
Park et al.

(10) Patent No.: US 6,436,698 B2
(45) Date of Patent: Aug. 20, 2002

(54) APPARATUS FOR AUTOMATIC MEASURING OF WATER TOXICITY

(75) Inventors: Han Oh Park; Hanee Park; Il Kyu Choi, all of Chungbok (KR)

(73) Assignee: Bioneer Corporation, Chungbuk (KR)

( * ) Notice: Subject to any disclaimer, the term of this patent is extended or adjusted under 35 U.S.C. 154(b) by 0 days.

(21) Appl. No.: 09/761,654

(22) Filed: Jan. 18, 2001

(30) Foreign Application Priority Data

Jan. 18, 2000 (KR) .......................................... 2000-2114
Jan. 15, 2001 (KR) .......................................... 2001-2101

(51) Int. Cl.[7] ................................................ C12M 1/36
(52) U.S. Cl. ................ 435/286.1; 435/286.5; 435/288.4; 435/288.7; 422/52
(58) Field of Search .......................... 422/52.81; 436/52, 436/286.1; 435/286.5, 287.1, 288.7, 288.4

(56) References Cited

U.S. PATENT DOCUMENTS

| | | | | |
|---|---|---|---|---|
| 4,772,453 A | * | 9/1988 | Lisenbee | 422/52 |
| 5,043,141 A | * | 8/1991 | Wilson et al. | 422/100 |
| 5,082,628 A | * | 1/1992 | Andreotti et al. | 250/361 C |
| 5,380,487 A | * | 1/1995 | Choperena et al. | 198/346.2 |
| 5,683,868 A | * | 11/1997 | LaRossa et al. | 435/252.33 |
| 5,798,263 A | * | 8/1998 | Wood et al. | 250/361 C |
| 6,017,722 A | * | 1/2000 | Becvar et al. | 210/658 |

* cited by examiner

*Primary Examiner*—David A. Redding
(74) *Attorney, Agent, or Firm*—Foley & Lardner

(57) ABSTRACT

The present invention relates to an apparatus for automatic measuring of water toxicity. More specifically, the present invention provides an apparatus for automatic and continuous measuring of water toxicity and/or contamination using luminescent microorganisms living in freshwater.

9 Claims, 4 Drawing Sheets

APPARATUS FOR AUTOMATIC MEASURING OF WATER TOXICITY

TECHNICAL FIELD OF THE INVENTION

The present invention relates to an apparatus for automatic measuring for water toxicity. More specifically, the present invention provides an apparatus measuring water toxicity and/or contamination continuously and automatically using luminescent microorganisms living in freshwater.

BACKGROUND OF THE INVENTION

A method using luminescent microorganisms is known to measure water toxicity and/or contamination. The luminescent mechanism of the luminescent microorganism is affected by activation of biochemical environmental conditions of the luciferase that controls the emission of light, resulting in changing luminosity of the microorganism. The Microtox Assay System (hereinafter, MAS) commercialized by the MICROBICS Co. is an apparatus measuring water toxicity and/or contamination using luminescent microorganisms. The MAS method measures the luminosity of light emitted by luminescent microorganism under toxic conditions on the basis of the luminosity of the luminescent microorganism living non-toxic conditions. The measuring value of MAS is $EC_{50}$ that represents concentration of toxic chemicals causing 50% reduction of luminosity.

However, because seawater microorganisms are used in MAS system, a separate addition of salts into a test sample in an amount equivalent to that of seawater is required to show physiological function of luminescent microorganisms. In this case, toxicity of chemicals may be offset due to the reaction of chemicals with metals and salts. As a result while most parts of the MAS data show similar results with those obtained from measurements using other microorganisms, the MAS toxicity data do not align with those obtained from measurements using other microorganism, for toxic chemicals such as ammonia or cyanide.

In addition, in order to measure toxicity of samples using MAS, lyophilized microorganisms contained in each ampoule need to be rehydrated one by one, and then are mixed with aqueous sample before their luminescence is measured by luminometer. Furthermore, MAS requires a batch operation system, wherein an operator measures luminescence of each individual sample manually. Therefore, in order to measure and observe the water toxicity continuously and continuously using a MAS method, an ampoule containing luminescent microorganisms needs each measuring time, which necessitate an operator for an apparatus measuring toxicity. Due to these problems, it has been a very laborious work to measure water toxicity continuously using the currently available apparatuses. Therefore, continuous monitor of water toxicity was almost impossible with any methods that have been developed up to now for the purpose of measuring water toxicity. Until the present invention, an automatic apparatus for measuring and monitoring water toxicity has never been developed. Despite of necessity and importance of continuous and automatic monitoring of water toxicity, automatic measurements are limited for pH, DO, water level, flow rate, and the like. Automatic measuring and monitoring of COD and SS is reported to be partially available for several limited samples.

Moreover, an environmental monitoring system is mainly limited to air pollution field. Thus, in water field, only monthly monitoring has been done in each water system, and continuous and automatic system for measuring and monitoring water pollution has not yet been commercialized.

SUMMARY OF THE INVENTION

Therefore, the present invention provides an apparatus for automatic and continuous measuring of water toxicity, comprising A sample supplier for gathering test samples from water system at regular intervals and continuously, and for supplying test samples to luminescent microorganisms;

- a multi-well plate containing luminescent microorganisms, wherein the top of the well is sealed with gas-impermeable film;
- a storage unit for multi-well plate, which sequentially supplies multi-well plates, wherein each well contains, lyophilized luminescent microorganisms;
- a transportation means for said multi-well plates;
- an injection needle for providing test samples and reagents in an accurate amount into luminescent microorganism contained said multi-well plate;
- a sensor for detecting luminosity after a lapse of certain times from injection of samples and reagents into luminescent microorganisms; and
- a control unit for electrical or mechanical control or regulation of an automatic operation of said each unit.

In addition, the apparatus of the present invention may further comprises a temperature control unit that controls and/or maintains constant temperature inside of the apparatus.

Therefore, one aspect of the present invention is to provide an apparatus capable of measuring water toxicity continuously without an operator.

Another aspect of the present invention is to provide a multi-well plate containing luminescent microorganisms, wherein top of the well is sealed with gas-impermeable film.

BRIEF DESCRIPTION OF THE DRAWINGS

The above aspects and other advantages of the present invention will become more apparent by describing in detail a preferred embodiment thereof with reference to the attached drawings, in which.

DETAILED DESCRIPTION OF THE INVENTION

Figure 1:
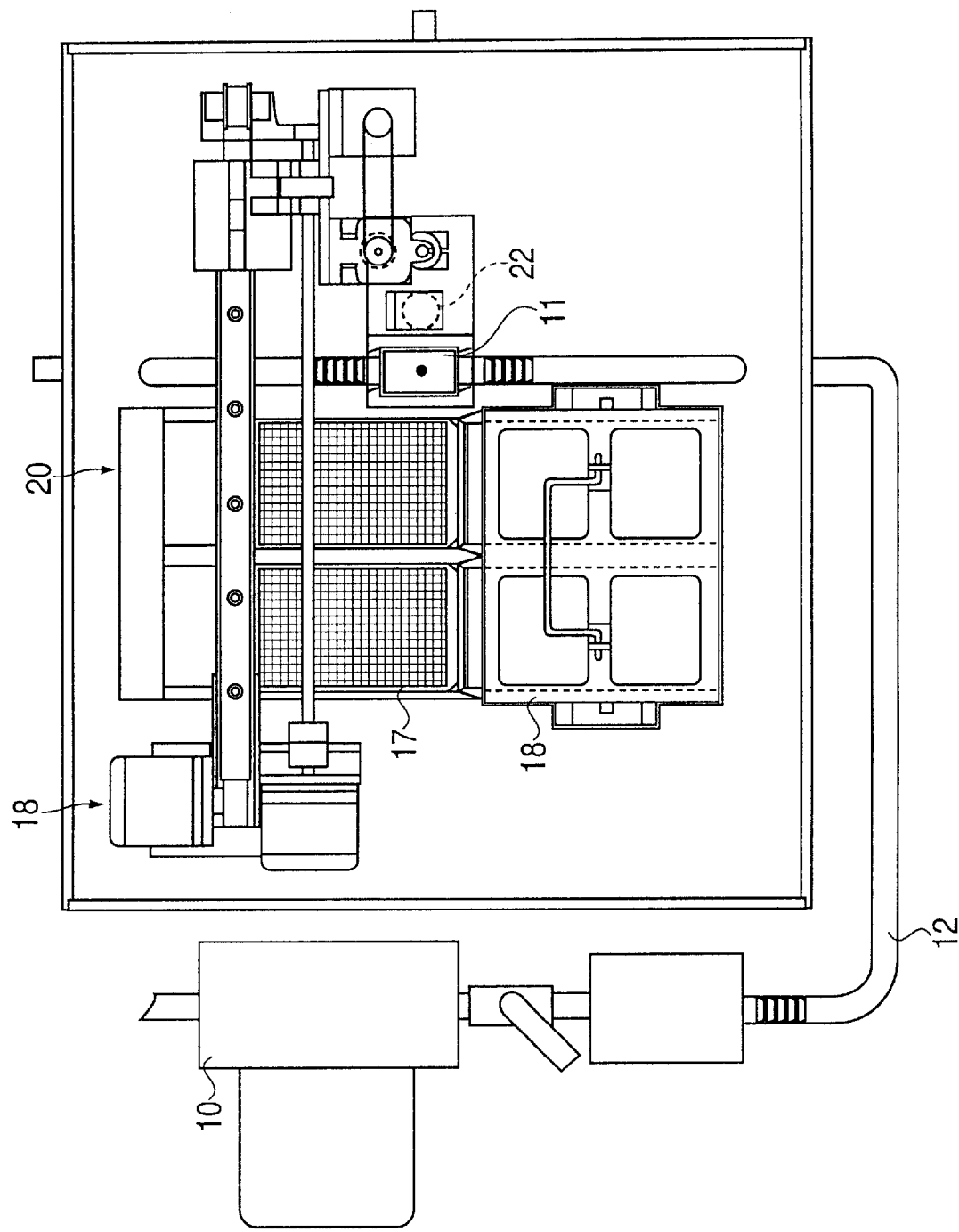
FIG. 1 is a front view of an apparatus for automatic measuring water toxicity.
Figure 2:
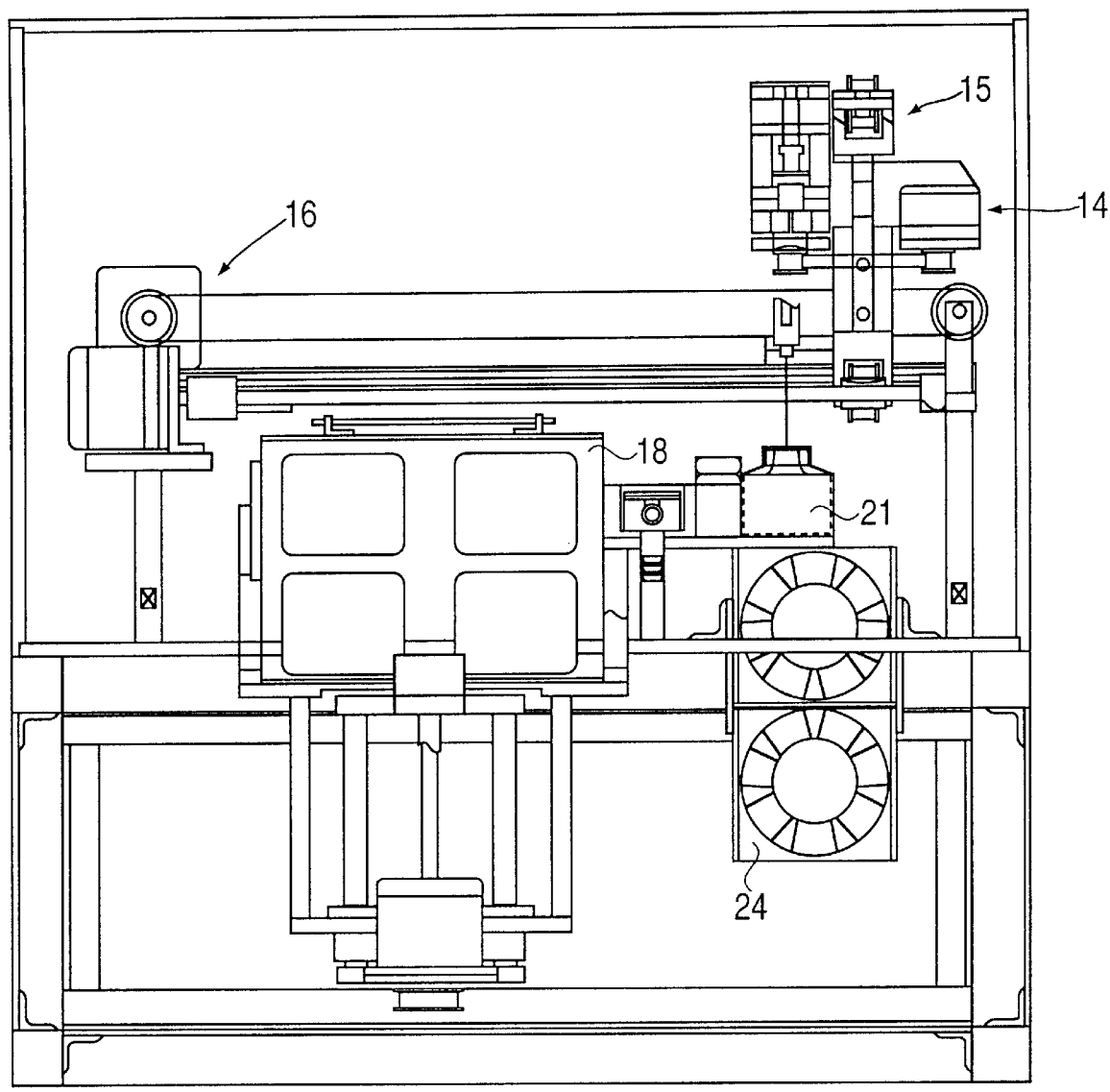
FIG. 2 is a plane view of an apparatus for automatic measuring water toxicity.
Figure 3:
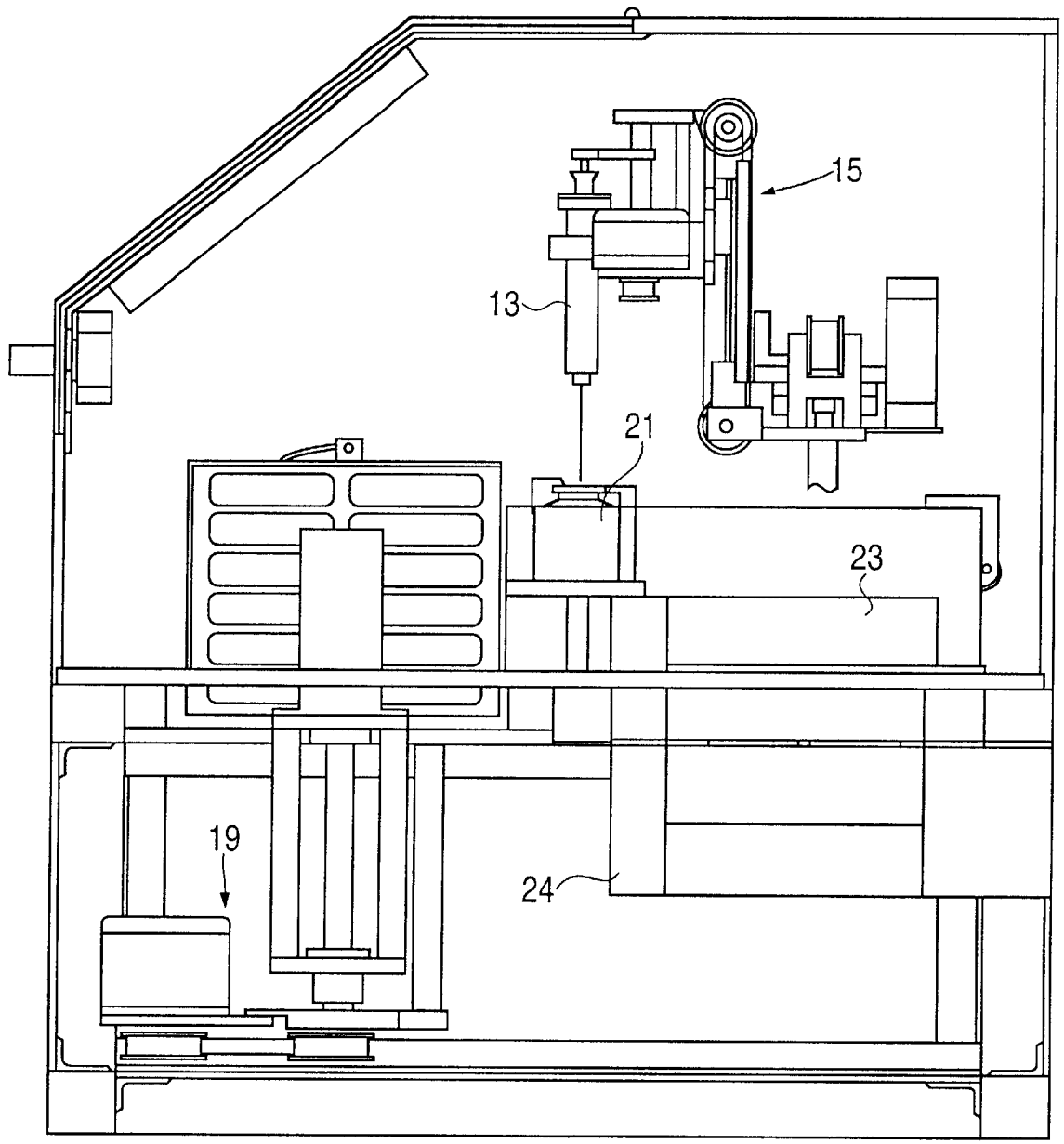
FIG. 3 is a right-side view of an apparatus for automatic measuring water toxicity.
Figure 4:
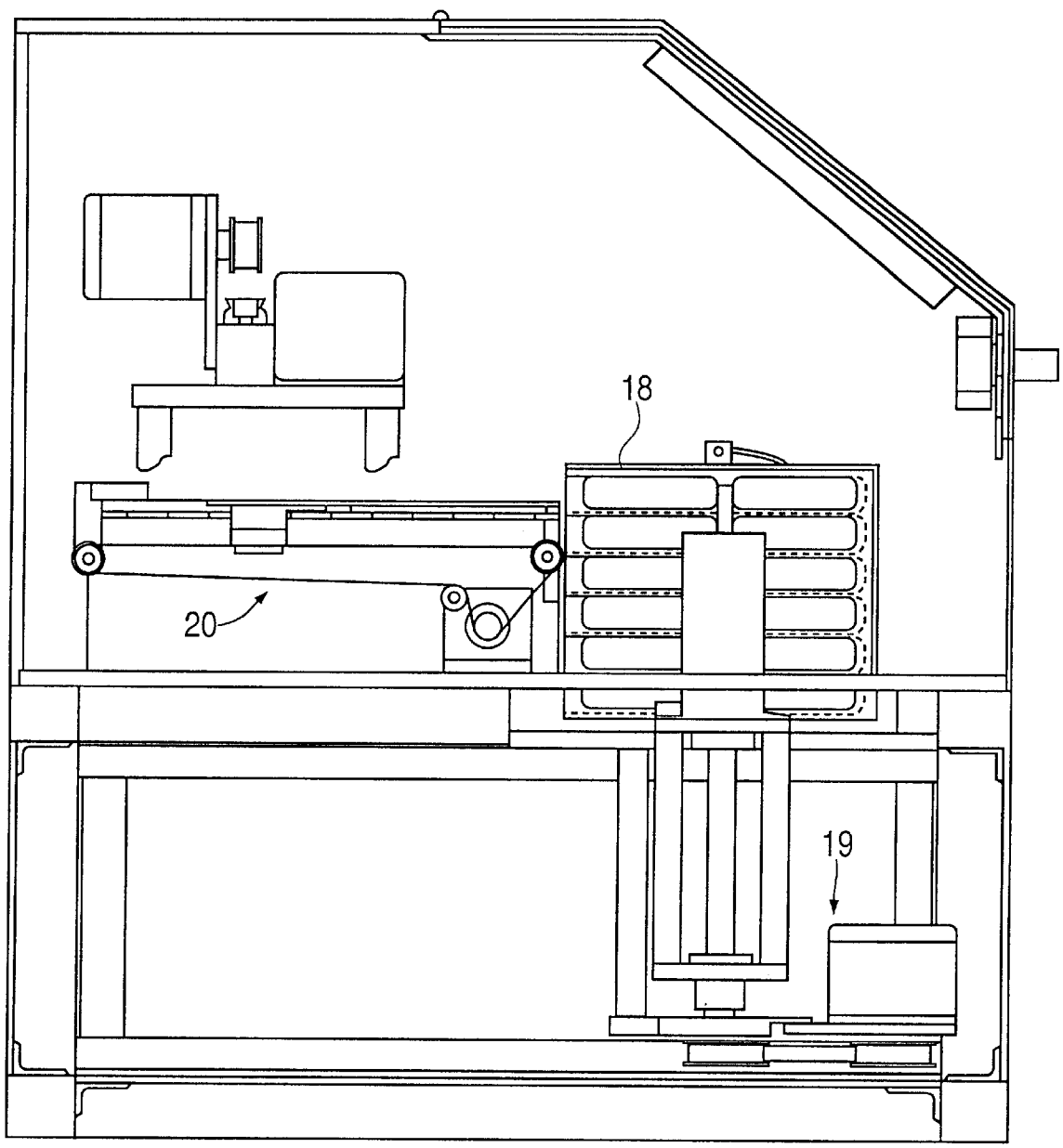
FIG. 4 is a left-side view of an apparatus for automatic measuring water toxicity.

Hereinafter, an apparatus of the present invention will be described in more detail. However, the automatic water toxicity measuring apparatus explained in below is given only for the explanation of embodiment of the present invention and not intended to limit the scope of the present invention.

An apparatus of the present invention for automatic measuring of water toxicity comprises:

- a sample supplier for gathering test samples from water system at regular intervals and continuously, and for supplying test samples to luminescent microorganisms;

a multi-well plate containing luminescent microorganisms, wherein the top of the well is sealed with gas-impermeable film;

a storage unit for multi-well plate, which sequentially supplies multi-well plates, wherein each well contains, lyophilized luminescent microorganisms;

a transportation means for said multi-well plates;

an injection needle for providing test samples and reagents in an accurate amount into luminescent microorganism contained said multi-well plate;

a sensor for detecting luminosity after a lapse of certain times from injection of samples and reagents into luminescent microorganisms; and a control unit for electrical or mechanical control or regulation of an automatic operation of said each unit.

In addition, the apparatus of the present invention may further comprises a temperature control unit that preferably employs Peltier device and heat radiation board as a temperature controls means.

The said sample supplier comprises a circulation pump, a sample-collecting block to collect aqueous samples from water system such as river, brook, lake, marshes, and etc., and a sample supplying tube. The said control unit initiates the circulation pump operation at preset-time intervals. Then the said circulation pump takes in the sample from water system through the sample supply tube. The aqueous sample collected by the said sample supplier is transferred into the injection needle by the operation of the said circulation pump through the sample supply tube. At the end of the sample supplying tube of the sample supplier, there is a filter that prevents entering of non-liquid substances and also, is an apparatus for creating reverse stream to prevent clogging of the said filter with the non-liquid substances.

The said storage unit for multi-well plate that stores and supplies the multi-well plates that contain lyophilized luminescent microorganism, comprises a rack which stores numerous multi-well plates in layers, an operation means which moves the said rack in up/down directions, and a transportation means that transport the multi-well plate in front/back directions in order to take out the multi-well plates.

The luminescent microorganism of the present invention may be the freshwater luminescent microorganism obtained preferably from freshwater or prepared by gene manipulation. The luminescent microorganisms are placed in each well of the multi-well plate and then lyophilized. The said well is purged with nitrogen, then the front of the plate is sealed with gas-impermeable film thereby securing the long-term preservation of the microorganism. The rack of the present invention can store numerous multi-well plates. The operation means for rack comprises a stepping motor and a ball screw. The rack is driven by the stepping motor to transport the multi-well plate in up/down directions thus desired plate can be selected. The transportation means for the multi-well plate is to bring out the plate from inside the rack and mounting the multi-well plate on the stage by moving the plate in front/back directions to desired positions. That is, the said transportation means adjusts the position of the multi-well plate wherein the reagent and test sample can be precisely injected on the desired well through the injection needle and wherein the sensor can precisely measure the luminosity of light emitted by the microorganism contained in desired well. The said transportation means comprises a pulley and belt mounted thereon, and a stepping motor connected with pulley through the belt, and by the operation of the belt driven by the stepping motor, the transportation means take out the multi-well plate from the rack.

The said injection needle comprises a syringe which takes in aqueous test sample and reagent from the sample supplier and reagent storage unit, and a piston operation means that control the amounts of test sample and reagents discharged. The said piston operation means comprises a stepping motor and a ball screw, a pulley and a belt to control the movement of piston through the operation of stepping motor. Therefore, the injected amount through the syringe of the present invention can be quantitatively controlled by the stepping motor to an extent of below $\mu l$. The position of the said syringe can be adjusted in up/down directions by means of pulley and the belt mounted thereon, ball spline and stepping motor, and thereby the movement of the syringe is driven by the operation of stepping motor. The transportation means for moving syringe and sensor in left/right directions comprises a pulley, a stepping motor, and a linear motion (LM) guide, and the syringe and the sensor unit move along with the LM guide by the operation of stepping motor. The syringe and the sensor of the present invention are formed in one body and set. Thus, the syringe and the sensor move in left/right directions at the same time.

The said reagent storage unit comprises some bottles containing various reagents and dilution buffer required for luminescence of microorganisms.

The said sensor unit comprises a sensor and an operation means thereof required for measuring light reduction and luminosity of the luminescent microorganisms. Preferably, photon multiplier tube (PMT) is employed as a sensor of the apparatus of the present invention. When the apparatus is open, the control unit cut off the PMT operation power to secure the PMT safety.

The apparatus of the present invention may further comprise a temperature control unit. The temperature control unit of the present invention preferably employs a Peltier device and a heat radiation board as a temperature control means. The internal temperature of the apparatus of the present invention should be maintained in a certain level to secure luminescent reaction and appropriate storage of microorganism and reagents. Since the internal temperature of the apparatus of the present invention should be constant continuously throughout the four (4) seasons, cooling during the summer season and heating during the winter season are required. Therefore, the apparatus of the present invention employs the Peltier device that can cool and/or heat as one device the interior of the apparatus, together with air circulation devices, to control the internal temperature of the apparatus.

A thermostatic system of the apparatus that ensure uniform temperature inside the apparatus, can minimize measuring error, which may be caused by temperature change, and also can secures long-term storage of microorganism.

The control unit of the apparatus of the present invention controls the operation of the stepping motors that control precise positions of each units, the analog-digital converter that converts the output data of sensor into digital data that can be acknowledged by the computer, various solenoid valve that convert electric signal into mechanical signal, the power supplier that supplies required DC power, the temperature sensor that measures the interior temperature of the apparatus and/or the power controller that controls the heat generated from Peltier device.

The control unit of the present invention comprises $\mu$-COM, SRAM, EEPROM, RS232C serial port, exterior sensor, and SRAM and EEPROM constitute memory unit.

The analog-digital converter of the present invention converts the analog output data of the sensor (PMT) into digital data, which can be acknowledged by the computer.

An automatic gain adjustment device is installed between the PMT sensor and the analog-digital converter in order to increase the applicability of the apparatus. That is, when the PMT output is weak, degree of gain is automatically increased, and contrarily when PMT output is strong, degree of gain is automatically reduced to maintain appropriate degree of gain. In the present invention, solenoid valves controlled by electronic signals generated from the said control unit, is used for selective operation of the circulation pump, PMT device, and the apparatus for creating reverse stream to prevent clogging of filter located at the end of the said sample supply tube.

The stepping motors of the apparatus rotate in accordance with the number of pulse inputted for purpose of the precise position control of each unit, and also are controlled by the control unit.

In the apparatus of the present invention, a graphic user interface(GUI) commercialized for a personal computer is employed. Thus, all information regarding to the operation status of the apparatus can be processed through the monitor screen of the computer. In addition, through the control unit, self-diagnosis, and detection of exterior environment change and respond thereto are processed automatically to secure the safety of the apparatus.

The apparatus of the present invention can be controlled remotely and/or automatically operates to measures toxicity of aqueous sample and processes the data obtained therefrom for a prescribed period, without the operator's manipulation by using reagents and luminescent microorganism stored in this apparatus.

Hereinafter, an embodiment of the apparatus of the present invention will be described in greater detail with reference to the following Figures. The Figures are given only for the illustrations of the invention and are not intended to limiting the scope of the present invention.

In a preferable embodiment of the apparatus of the present invention, the test sample supplier comprises a circulation pump (10), a sample-collecting block (11) to collect aqueous samples from water system such as river, brook, lake, marshes, and etc., and a sample supplying tube (12). The control unit initiates the circulation pump (11) operation at preset-time intervals. Then the said circulation pump takes in test samples from water system. The aqueous sample collected by the said test sample supplier is transferred into an injection needle by the operation of the said circulation pump (10) through the sample supplying tube (12). At the end of the sample supply tube of the said sample supplier, there is a filter that prevents entering of non-liquid substances and also, is an apparatus for creating reverse stream to prevent clogging of the said filter with the non-liquid substances.

The said storage unit for multi-well plate (17 that stores and supplies the multi-well plates that contain lyophilized luminescent microorganism, comprises a rack (18) which stores numerous multi-well plates (17) in layers, an operation means (19) which moves the said rack in up/down directions, and a transportation means (20) that transport the multi-well plate (17) in front/back directions in order to take out the multi-well plates.

The luminescent microorganisms of the present invention may be the freshwater luminescent microorganisms obtained preferably from freshwater or prepared by gene manipulation. The luminescent microorganisms are set in each well of the multi-well plate and then lyophilized. The said well is purged with nitrogen then the top of the plate is sealed with gas-impermeable film thereby securing the long-term preservation of the microorganism. The rack of the present invention can store numerous multi-well plates. The operation means of rack comprises a stepping motor and a ball screw. The rack is driven by the stepping motor to transport the multi-well plate in up/down directions thus desired plate can be selected. The transportation means for the multi-well plate is to bring out the plate from inside the rack and mounting the multi-well plate on the stage by moving the plate in front/back directions to desired positions. That is, the said transportation means adjusts the position of the multi-well plate wherein the reagent and test sample can be precisely injected on the desired well through the injection needle and wherein the sensor can precisely measure the luminosity of light emitted by the microorganism contained in desired well. The said transportation means comprises a pulley and belt mounted thereon, and a stepping motor connected with pulley through the belt, and by the operation of the belt driven by the stepping motor, the transportation means take out the multi-well plate from the rack.

The said injection needle comprises a syringe (13) which takes in aqueous test sample and reagent from sample supplier and reagent storage unit, a piston operation means (14) that control the amounts of test sample and reagents discharged, and a syringe transportation means (15, 16). The said piston operation means (14) comprises a stepping motor and ball screw, a pulley and belt to control the movement of piston through the operation of stepping motor. Therefore, the injected amount through the syringe of the present invention can be quantitatively controlled by the control of the stepping motor to an extent of below $\mu l$. The position of the said syringe can be adjusted in up/down directions by the means (15) comprises a pulley and the belt mounted thereon, ball spline and a stepping motor, and thereby the movement of the syringe is driven by the operation of stepping motor. The transportation means (16) for moving syringe and sensor in left/right directions comprises a pulley, a stepping motor, and a linear motion (LM) guide, and the syringe and the sensor unit move along with the LM guide by the operation of stepping motor. The syringe and the sensor of the present invention are formed in one body and set. Thus, the syringe and the sensor move in left/right directions at the same time.

The luminescent microorganism used in the present invention may be freshwater luminescent microorganism separated from freshwater is desirable (Kim, E. -C., T. -S. Byun, K. -J. Park, and K. -H. Lee, 1998, Toxicity Test Using a Luminescently Transformed Bacterium with an highly Increased Sensitivity, The $38^{th}$ Korea Microorganism Scholarly Symposium and Spring Plenary Session; Park, K. -J., S. -J. Chun and K. -H. Lee, (1997), Development of toxicity test system using a Luminescently transformed freshwater bacterium $52^{nd}$ Korean As. Biol. Sci., Chunbuk Univ.).

In addition, the luminescent microorganisms used in the apparatus of the present invention, all luminescent microorganisms that can be luminous on contact with chemical substances, can be used. These luminescent microorganisms are natural or prepared by gene manipulation. Various luminescent microorganisms may be employed in the apparatus of the present invention can be obtainable from microorganism depository throughout the world. Especially, YH9-RC unit of which accession number is KCTC 0730BP is preferable. The appropriate luminescent microorganisms used in the apparatus of the present invention and the proliferation method thereof are described in detail in Korea Patent Application No. 2000-010763. Also, the method of lyophilizing luminescent microorganism used in the apparatus of the present invention is described in the Korea Patent Application No. 2000-37709.

In order to operate the apparatus of the present invention as long term-automated system, the rack stores numerous multi-well plates as like 384 well plate.

In order to arrange numerous plates efficiently, and to minimize the size of the apparatus, the preferred embodiment of the present invention employs rack structure wherein six (6) or more 384 well plates can be layered in two (2) row.

In case that the aqueous sample is tested every 10 minutes, 4,320 [6×24(hours)×30(days)] of wells which contains luminescent microorganism are required to measure and monitor water toxicity for one (1) month. Since the apparatus of the present invention can store twelve (12) or more of 384 well plates, 4,608 [384×12] or more of aqueous samples can be measured. The rest of well [4,608−4,320= 288] can be used as control.

Thus, 24 wells can be used as control well per each 384 well plate. In preferred embodiment of the present invention, twelve (12) or more of 384 well are set in the apparatus. Therefore, upon measuring aqueous sample every 10 minutes, automatic operation of the apparatus for one (1) month is possible. By supplying multi-well plates every one (1) month, automatic continuous water toxicity monitoring can be achieved.

The solution storage unit of the apparatus of the present invention stores bottles (21) that are containing reagents, dilution solution required for the activation of the luminescent microorganisms.

The sensor unit includes sensor (22) and operation means thereof, and the light reduction degree and luminosity of light emitted from luminescent microorganism is measured. Photon Multiplier Tube (PMT) is appropriately employed as the sensor device. The temperature control means of the present invention employs two (2) Peltier devices (23) and heat radiation board (24).

INDUSTRIAL APPLICABILITY

The apparatus for automatic measuring of water toxicity of the present invention comprises a test sample supplier for gathering test samples from water system at regular intervals and continuously and for supplying test sample to luminescent microorganism, a multi-well plate storage that keep and provide sequentially multi-well plate in which each well contains lyophilized luminescent microorganism, a transportation means for moving said numerous multi-well plates sequentially, an injection needle for providing test samples and reagents in an accurate dose into luminescent microorganism contained in said multi-well plate and a sensor for detecting luminosity after the lapse of some times from injection of test sample and reagent into luminescent microorganism, and a control unit that controls or regulates electrically or mechanically the operation of said each unit automatically.

By using the apparatus of the present invention, toxicity and contamination of water system can be measured continuously without operator's manipulation until the reagents and luminescent microorganism stored in this apparatus are consumed.

In addition, by supplying multi-well plates periodically, automatic and continuous water toxicity monitoring can be achieved.

In conclusion, the automatic water toxicity measuring apparatus of the present invention is appropriate to be employed as a terminal for remote monitoring of the water toxicity.

While the present invention has been particularly shown and described with reference to particular embodiment thereof, it will be understood by those skilled in the art that various changes in form and details may be effected therein without departing from the spirit and scope of the invention as defined by the appended claims.

This application claims priority from the Korean Patent Application No. 10-2000-0002114, the contents of which are hereby incorporated by reference in their entirety, including the specification, drawings and claims.

What is claimed is:

1. An apparatus for automatic and continuous measuring of water toxicity, comprising a sample supplier for gathering test samples from a water system at regular intervals and continuously, and for supplying test samples to luminescent microorganisms;

a multi-well plate containing luminescent microorganisms, wherein the top of the well is sealed with a gas-impermeable film;

a storage unit for said multi-well plates, which sequentially supplies said multi-well plates, wherein each well contains lyophilized luminescent microorganisms;

a transportation means for said multi-well plates;

an injection needle for providing test samples and reagents in an accurate amount into luminescent microorganisms contained in said multi-well plate;

a sensor for detecting luminosity after a lapse of certain times from injection of samples and reagents into luminescent microorganisms; and a control unit for electrical or mechanical control or regulation of an automatic operation of said apparatus.

2. The apparatus according to claim 1, wherein said sample supplier comprises a circulation pump, a sample collecting block for collecting aqueous samples, and a sample supplying tube.

3. The apparatus according to claim 1, wherein said luminescent microorganisms are freshwater luminescent microorganisms obtained from freshwater.

4. The apparatus according to claim 1, wherein said luminescent microorganisms are freshwater luminescent microorganisms prepared by gene manipulation.

5. The apparatus according to claim 1, wherein said storage unit for multi-well plates comprises a rack that stores multi-well plates in layers, an operation means that moves the said multi-well plates in up/down directions, and a transportation means that transport the said multi-well plates in front/back directions from the rack.

6. The apparatus according to claim 1, wherein said injection needle comprises a syringe which takes in an aqueous test sample and reagent from a sample supplier and a reagent storage unit, a piston operation means that control the amounts output by the said syringe, a transportation means for moving syringe.

7. The apparatus according to claim 1, further comprising a temperature control means for maintaining constant temperature inside the apparatus.

8. The apparatus according to claim 1, wherein the end of the sample supplying tube in the sample supplier comprises a filter that prevents entering of non-liquid substances and an apparatus that creates reverse stream to prevent clogging.

9. The apparatus according to claim 2, wherein the end of the sample supplying tube in the sample supplier comprises a filter that prevents entering of non-liquid substances and an apparatus that creates reverse stream to prevent clogging.

* * * * *